(12) United States Patent
Bouchoucha (10) Patent No.: US 11,160,471 B2
(45) Date of Patent: Nov. 2, 2021

(54) DEVICE SUITABLE FOR BEING INGESTED AND ASSOCIATED SYSTEM

(71) Applicants: Universite Paris Descartes, Paris (FR); Assistance Publique—Hopitaux de Paris, Paris (FR)

(72) Inventor: Michel Bouchoucha, Paris (FR)

(73) Assignees: UNIVERSITE PARIS DESCARTES, Paris (FR); ASSISTANCE PUBLIQUE—HOPITAUX DE PARIS, Paris (FR)

( * ) Notice: Subject to any disclaimer, the term of this patent is extended or adjusted under 35 U.S.C. 154(b) by 283 days.

(21) Appl. No.: 15/574,132

(22) PCT Filed: May 13, 2016

(86) PCT No.: PCT/EP2016/060924
§ 371 (c)(1),
(2) Date: Nov. 14, 2017

(87) PCT Pub. No.: WO2016/184821
PCT Pub. Date: Nov. 24, 2016

(65) Prior Publication Data
US 2018/0125390 A1 May 10, 2018

(30) Foreign Application Priority Data
May 15, 2015 (FR) ........................ 1554376

(51) Int. Cl.
*A61B 5/07* (2006.01)
*A61B 5/00* (2006.01)
*A61B 5/06* (2006.01)
(52) U.S. Cl.
CPC .............. *A61B 5/073* (2013.01); *A61B 5/061* (2013.01); *A61B 5/4255* (2013.01); *A61B 5/6861* (2013.01)

(58) Field of Classification Search
CPC .. A61B 5/00; A61B 5/07; A61B 5/073; A61B 5/42; A61B 5/4222; A61B 5/4255;
(Continued)

(56) References Cited

U.S. PATENT DOCUMENTS

| 6,904,308 B2 * | 6/2005 | Frisch | A61B 1/041 |
| | | | 600/424 |
| 7,427,266 B2 * | 9/2008 | Ayer | A61B 5/073 |
| | | | 600/302 |

(Continued)

OTHER PUBLICATIONS

DeSesso, J. M., & Jacobson, C. F. (2001). Anatomical and physiological parameters affecting gastrointestinal absorption in humans and rats. Food and chemical toxicology, 39(3), 209-228. (Year: 2001).*

(Continued)

*Primary Examiner* — Devin B Henson
(74) *Attorney, Agent, or Firm* — Womble Bond Dickinson (US) LLP (57) ABSTRACT

A device for being ingested by a patient, which includes a disintegration matrix designed to disintegrate in a digestive segment and a plurality of independent passive RFID markers that are housed together in the disintegration matrix. The disintegration matrix isshaped so that when it disintegrates, the RFID markers separate from one another and are no longer mechanically connected, so that each RFID marker is able to move independently of the other RFID markers in several segments of the digestive system of the patient. The RFID markers each being, in the disintegration matrix, protected by a hermetic encapsulation in a biocompatible material.

16 Claims, 4 Drawing Sheets

(58) Field of Classification Search
CPC ....... A61B 5/68; A61B 5/6846; A61B 5/6847; A61B 5/6861; A61B 5/061
See application file for complete search history.

(56) References Cited

U.S. PATENT DOCUMENTS

| | | | | |
|---|---|---|---|---|
| 10,045,713 B2* | 8/2018 | Old | ........................ | A61B 5/061 |
| 2005/0063906 A1* | 3/2005 | Kraizer | .................. | A61B 5/073 |
| | | | | 424/9.1 |
| 2006/0122494 A1* | 6/2006 | Bouchoucha | .......... | A61B 1/041 |
| | | | | 600/424 |
| 2006/0289640 A1* | 12/2006 | Mercure | .............. | A01K 11/007 |
| | | | | 235/435 |
| 2009/0009332 A1* | 1/2009 | Nunez | ...................... | A61D 7/00 |
| | | | | 340/572.1 |
| 2014/0309505 A1* | 10/2014 | Euliano | ................ | A61B 5/4833 |
| | | | | 600/302 |
| 2016/0270639 A1* | 9/2016 | Trollsas | ............... | A61B 1/2736 |

OTHER PUBLICATIONS

Aug. 2014) "TRPGR30ATGC 12-mm Low-Frequency Glass-Encapsulated Transponder, Read Only" TI.com. Retrieved from http://www.ti.com/lit/ds/symlink/trpgr30atgc.pdf (Year: 2014).*

Jia, X., Feng, Q., Fan, T., & Lei, Q. (Apr. 2012). Analysis of anti-collision protocols for RFID tag identification. In 2012 2nd International conference on consumer electronics, communications and networks (CECNet) (pp. 877-880). IEEE. (Year: 2012).*

* cited by examiner

| Antenna 1 Number of markers 2 | Antenna 2 Number of markers 3 | Antenna 3 Number of markers 2 | Antenna 4 Number of markers 0 |
|---|---|---|---|
| Antenna 5 Number of markers 3 | Antenna 6 Number of markers 0 | Antenna 7 Number of markers 1 | Antenna 8 Number of markers 0 |
| Antenna 9 Number of markers 1 | Antenna 10 Number of markers 2 | Antenna 11 Number of markers 2 | Antenna 12 Number of markers 0 |
| Antenna 13 Number of markers 1 | Antenna 14 Number of markers 2 | Antenna 15 Number of markers 2 | Antenna 16 Number of markers 0 |
| Antenna 17 Number of markers 0 | Antenna 18 Number of markers 0 | Antenna 19 Number of markers 0 | Antenna 20 Number of markers 0 |

DEVICE SUITABLE FOR BEING INGESTED AND ASSOCIATED SYSTEM

TECHNICAL FIELD

The invention relates to the technical field of devices suitable for being ingested by a subject and used by a detection assembly within the scope of measurements such as transit measurements in the digestive system of a subject.

PRIOR ART

It is possible to use different techniques to measure digestive transit.

Scintigraphic techniques are used mainly to measure gastric emptying, but it is also possible to measure the intestinal transit time or the colonic transit time.

In the case of the measurement of the gastric emptying time, the decrease of a marker from a meal phase, solid or liquid, is measured. The radio-pharmaceutical used is specific to the phase to mark. For example, to measure the gastric emptying of the digestible solid phase, it is possible to use an omelette in which the ovalbumin is marked in vitro by 40 MBq of technetium-rhenium sulphide whereas, to measure the gastric emptying of the liquid phase, it is possible to use a non-absorbable radiopharmaceutical, indium 111 ($^{111}$In)-DTPA (5.5 MBq). The protocol is complex. It comprises several steps:

- Double window acquisition (140 keV for $^{99m}$Tc and 245 keV for $^{111}$In): anterior and posterior multistatic abdominal acquisitions each of 1 minute and separated by a rest interval of 13 minutes. The patient, in standing position at the moment the images are taken, can sit down during rest periods.
- Plotting a region of interest (ROI) around the stomach, incidence by incidence and image by image; plotting of a paragastric ROI in such a way as to subtract the background noise from the untreated activity coming from the gastric region of interest.
- Plotting residual gastric activity curves for each of the solid and liquid phases.
- Analysis for the determination of functional parameters such as the half-emptying time defined by the elimination of 50% of the activity of each of the phases.

Isotopic techniques for measuring intestinal and colonic transit times are even more complex with the definition of numerous zones of interest and the use of different radiopharmaceuticals.

Radiological techniques use radio-opaque markers. These markers are ingested by the patient and may be detected by radiography to carry out transit measurements, mainly the measurement of the colonic transit time.

Several ingestion protocols for radiological techniques may be used:

- The "Single marker-Single ingestion-Multiple films" method has been proposed by Arhan et al. (Arhan, P., et al., Segmental colonic transit time. Dis Colon Rectum, 1981. 24(8): p. 625-9): 20 radio-opaque markers are ingested in the morning and abdominal radiographies are carried out at 24 hour intervals up to elimination of all the markers.
- A simplified version of the test ("Single ingestion-Single marker-Single film") involves an abdominal radiography on the seventh day after the ingestion of the markers in order to determine not the colonic transit time, but the existence of a transit delay (Bouchoucha, M., et al., What is the meaning of colorectal transit time measurement? Dis Colon Rectum, 1992. 35(8): p. 773-82).
- Another approach for the measurement of the total and segmental colonic transit ("Multiple markers-Multiple ingestions-Multiple films"), described by Metcalf et al. (Metcalf, A. M., et al., Simplified assessment of segmental colonic transit. Gastroenterology, 1987. 92(1): p. 40-7) and Chaussade et al. (Chaussade, S., et al., Mesure du temps de transit colique (TTC): description et validation d'une nouvelle technique. Gastroenterol Clin Biol, 1986. 10(5): p. 385-9), involves the ingestion of different radio-opaque markers each day at the same time for 3 consecutive days. An abdominal radiography is taken at the ingestion time on the fourth day of the study, then at intervals of 3 days (7 days, 10 days, etc.) up to elimination of all the markers.

Today the measurement of the colonic transit time using radio-opaque markers is based on the hypothesis of a stable state during the measurement. In these conditions, the elimination of the markers takes place at the same speed whatever the day of ingestion (Bouchoucha, M., et al., What is the meaning of colorectal transit time measurement? Dis Colon Rectum, 1992. 35(8): p. 773-82). This method ("Single marker-Multiple ingestion-Single film") makes it possible to measure the colonic transit time using a simple abdomen without preparation (AWP) on the lying down side, carried out after daily ingestion of 12 radio-opaque markers for 6 days (Bouchoucha, M., et al., What is the meaning of colorectal transit time measurement? Dis Colon Rectum, 1992. 35(8): p. 773-82). This "gold standard" makes it possible to determine oral-anal transit and segmental transit in the right colon, the left colon and the terminal bowel or rectosigmoid. This method, based on the hypothesis of a stable state, makes it possible to dispense with carrying out daily radiographies (Martelli, H., et al., Some parameters of large bowel motility in normal man. Gastroenterology, 1978. 75(4): p. 612-8; Martelli, H., et al., Mechanisms of idiopathic constipation: outlet obstruction. Gastroenterology, 1978. 75(4): p. 623-31) and markers of different types (Chaussade, S., et al., Mesure du temps de transit colique (TTC): description et validation d'une nouvelle technique. Gastroenterol Clin Biol, 1986. 10(5): p. 385-9).

These techniques may also be used to measure the gastric emptying time by defining the zone of interest by projection of the stomach (Bertrand J et al. Etude du temps d'evacuation gastrique de repos normaux au moyen de granules radio-opaques. Applications cliniques et validation. Gastroenterol Clin Biol: 1980; 11; 4: 770-6).

However, the methods of using these systems require specific instrumentation and involve regular irradiation of the patient. They are thus cumbersome to implement and potentially dangerous to health on account of the level of irradiation to which the patient is subjected. Moreover, their precision is limited due to the importance of physiological variations (dietary intake, physical activity, stress, etc.). Moreover, the repetition of these examinations is limited due to the irradiation, which limits their interest in the evaluation of a treatment.

Furthermore, it is possible to monitor the ingestion of an ingested marker, of Smartpill™ or Motilis™ type, and to monitor its evolution in the digestive system. This marker may be detected by the positioning of a magnetic, Motilis™, or radiofrequency, Smartpill™, field emitted. Nevertheless, these markers do not enable monitoring representative of transit time, do not enable the measurement of segmental colonic transit and are sensitive to external perturbations thereby restricting their use in outpatient care.

The document US2009/009332 relates to a device that uses "RFID tags" (that is to say RFID markers) to evaluate the observance of the patient in a context of medication. In this patent application, the RFID tag is attached totally or partially to the medicine in solid form (hard capsule, tablet, etc.). Several tags may be used. The tag may be detected through the body of the patient by a system composed of one or more antennas. The medicine/tag "complex" is coated with one or more layers having the characteristic of disintegrating in the gastro-intestinal system. The intestinal absorption of the medicine and the pharmacological aim of this system do not allow its use with an aim of physiological exploration of colonic transit.

The document US2006/169292 relates to a system making it possible to detect within a human body a device that has been ingested, such as a capsule comprising a type of probe (pH, temperature, pressure, etc.), and referred to as intelligent. This device is active, because it benefits from batteries in order to be able to operate. RFID tags may be used and included in a capsule in order to monitor the movement of the capsule through the human body, which does not advance at the speed of the chyme. A single capsule is ingested by the patient. This system thus does not make it possible to assess the dispersion of an ingested bolus or to measure a total or segmental colonic transit time.

The devices described in these documents are not designed to enable a measurement of the total and segmental colonic transit times.

DESCRIPTION

One aim of the invention is to overcome at least one of the aforesaid drawbacks.

One aim of the invention is thereby in particular to propose a system having fewer health risks for the patient while enabling good detection sensitivity.

To this end, a device suitable for being ingested by a patient is provided, the device comprising a plurality of independent RFID markers held together by a disintegration matrix that is designed to disintegrate in a determined digestive segment.

The invention according to this aspect is advantageously completed by the following features, taken alone or in any technically possible combinations thereof:
  the device takes the form of a hard capsule, a pessary or any other presentation enabling oral ingestion;
  the matrix comprises a coating enabling disintegration in a zone of interest dependent on the measurement to carry out, for example a coating sensitive to acid pH, for example disintegrating at pHs less than 6, for gastric disintegration;
  the device comprises at least two RFID markers, preferably more than 5 RFID markers;
  the RFID markers have a density of 1.20 to 1.70 comparable to that of the digestive chyme; the density corresponds to the specific gravity of the marker with respect to the specific gravity of water;
  the RFID markers have at least one dimension less than or equal to 15 mm, preferably less than or equal to 5 mm, preferably less than or equal to 4 mm;
  the RFID markers have dimensions such that the largest dimension of each RFID marker is less than or equal to 15 mm and/or the smallest dimension of each RFID marker is less than or equal to 3 mm;
  each RFID marker differs from the other RFID markers of the plurality of RFID markers by a characteristic to differentiate each RFID marker from the other RFID markers of the plurality of RFID markers;
  the RFID markers comprise anticollision means;
  the RFID markers have a frequency less than or equal to 135 kHz;
  the RFID markers comprise
    a substrate and/or
    an encapsulation;
  the RFID markers are passive RFID markers;
  the substrate or the encapsulation are composed of a biocompatible material;
  the RFID markers do not comprise a battery.

The invention further relates to a RFID signal detection assembly suitable for covering a part of the body of a patient, the detection assembly comprising a support and a plurality of RFID antennas (namely antennas having the capability of remotely activating a RFID marker and receiving the identification carried by this RFID marker) fixed to the support so as to form a network, the network being suitable for identifying, when said support (22) covers the part of the body of the patient, the RFID markers (11) ingested by a patient.

The invention according to this aspect is advantageously completed by the following features, taken alone or in any of the technically possible combinations thereof:
  the support has a shape that may be modified to hug the shape of the part of the body of the patient;
  the support is flexible;
  each antenna of the plurality of RFID antennas is suitable to be connected to a same reading means so as to form a single RFID reader;
  the plurality of antennas is composed of at least three RFID antennas, preferably more than six RFID antennas;
  the support comprises a longitudinal axis placed at the centre of the support;
  the support is hypoallergenic and/or biocompatible;
  the support comprises a protective layer from external electromagnetic interference;
  the RFID antenna have a predetermined transmission/reception range and are arranged in such a way that the network enables at least one transmission/reception range overlap zone;
  the RFID antennas are multidirectional antennas.

The invention further relates to a system comprising:
  at least one device such as described previously,
  a detection assembly suitable for identifying the RFID markers of the device after ingestion by the patient of the device, and
  computing means suitable for determining, by means of the detection assembly and after ingestion by the patient of the device, a spatial distribution of RFID markers of the device in several segments of the digestive system so as to enable the counting of the RFID markers for each segment of the digestive system, the digestive segments being the digestive segment where there is disintegration and those situated after or before with respect to the direction of advancement of the chyme.

The invention according to this aspect is advantageously completed by the following features, taken alone or in any of the technically possible combinations thereof:
- at least one other RFID marker suitable for being positioned on the body of the patient to calibrate the position of the detection assembly;
- the computing means are configured to determine a measurement of the digestive transit time of the patient;
- the computing means are configured to determine a representation of the digestive transit of the patient;
- a signal reflecting surface is placed on another part of the body of the patient, preferably being continuous with the support.

The invention further relates to a system comprising:
- a plurality of RFID markers,
- a detection assembly such as described previously, and
- computing means suitable for determining, when the support covers a part of the body of the patient and after ingestion by the patient, a spatial distribution of RFID markers of the device in the part of the body of the patient.

The invention according to this aspect is advantageously completed by the following features, taken alone or in any technically possible combinations thereof:
- at least one other RFID marker suitable for being positioned on the body of the patient to calibrate the position of the detection assembly;
- the computing means are configured to determine a measurement of the digestive transit time of the patient;
- the computing means are configured to determine a representation of the digestive transit of the patient;
- a signal reflecting surface is placed on another part of the body of the patient, preferably being continuous with the support.

The invention further relates to a measurement method implemented by means of a system such as described previously, comprising:
- positioning the support so as to cover a part of the body of the patient; and
- the reception, by the network, of RFID signals transmitted by the RFID markers;
- the determination by the computing means of the spatial distribution of the RFID markers in the part of the body of the patient.

DRAWINGS

Other objectives, features and advantages will become clear from reading the description that follows given for illustrative purposes and non-limiting, with reference to the drawings, among which.

DESCRIPTION

Device

Figure 1:
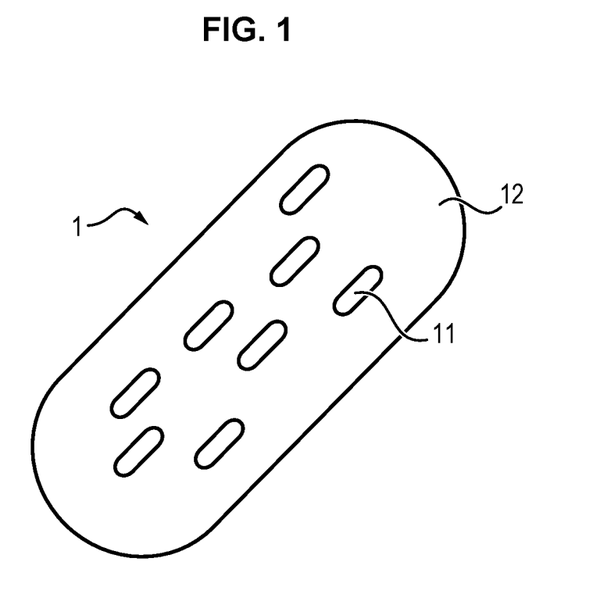
FIG. 1 represents a device according to an exemplary embodiment of the invention.

FIG. 1 represents a device 1 according to one exemplary embodiment of the invention.

General Structure of the Device

The device is suitable for being ingested by a patient. The device may form a hard capsule, a pessary, a capsule, a tablet or any other presentation enabling ingestion by oral route by a patient.

The device comprises a plurality of independent RFID markers 11. The RFID markers 11 of the plurality of RFID markers are held together by a disintegration matrix 12 that is designed to disintegrate in a digestive segment, for example gastric, intestinal or colonic disintegration, making it possible to release the RFID markers 11 which move freely in several parts of the digestive system of the person. The RFID markers 11 are not totally or partially attached to the matrix 12 and thereby differ from the prior art (US2009/009332).

Independent is typically taken to mean that each RFID marker 11 is distinct from the other RFID markers 11 and that once the matrix 12 has disintegrated, the RFID markers 11 are separated from each other and are no longer mechanically connected, so that each RFID marker 11 can be moved independently of the other RFID markers 11, with the digestive chyme, in the segments of the digestive system.

"RFID markers" is taken to mean RFID transponders which here enable the analysis of the colonic transit and which are not associated with any other internal physiological measurement sensor, such as pH, temperature, or others, or with a medicine. The device 1 thereby differs from the prior art (US 2006/169292).

On the other hand, the RFID markers are free to move with respect to each other in the digestive segments or parts of the digestive system which are observed by the medical personnel.

In an advantageous embodiment, the RFID markers are free to move with respect to each other also in the matrix 12.

Such a device may thereby be ingested by the patient, following which the disintegration of the matrix 12 enables the release of the RFID markers 11 at the desired moment. These RFID markers 11 may then be detected by methods as described for example hereafter.

The device 1 as such is not dangerous to health, and the associated measuring method also has greatly reduced health risks compared to those generated by measurement methods using isotopic or radio-opaque markers. This makes it possible to limit the ionising irradiation of the patient because no radiography is required to detect the RFID markers 11. In particular, the irradiation of the RFID markers 11 may be limited to an irradiation comparable to that of a radio receiver.

Moreover, compared to radio-opaque markers, the RFID markers 11 are easier to differentiate and cannot be confused with arterial or bone calcifications.

This device 1 is not based on magnetic field detection. Its detection may thus be implemented in outpatient care because unlike magnetic field detection, it is not sensitive to environmental electromagnetic perturbations. Furthermore, unlike methods based on the use of scintigraphic markers or radio-opaque markers, it does not require bulky equipment.

Moreover, the device 1 may be implemented using passive RFID markers. It is thereby possible not to use a battery, which enables the device to be made less bulky and less polluting. Moreover, the device 1 may thereby not rely on the use of a battery.

Its simplicity and its low level of dangerousness enable the use of this device for pregnant women or child patients. Moreover, the measurement associated with this device 1 may be carried out by an attending physician, general practitioner or gastroenterologist, without requiring the presence of other specialists (radiologist, nuclear medicine).

Since this device 1 and its detection do not pose any health risk, it is possible to ingest several thereof at determined time intervals and to carry out regular measurements so as to obtain mean measurements and thus be free of variations in transit from one day to the next, which may be linked to diet, to physical activity or instead to other factors such as stress.

The fact that the device 1 comprises the plurality of RFID markers 11 in the disintegration matrix 12 also makes it possible to have a measurement that is less sensitive to variations due to factors which may have an influence on the digestive transit, in particular compared to a single marker.

The RFID markers 11 may be of small size and resorting to such markers makes it possible to use a considerable number thereof for a device 1 which remains of sufficiently small size to be ingested without difficulty.

Such regular intake is all the easier when the device, by virtue of its shape, may be ingested like a medicine.

This device 1 may in particular be suitable for making it possible to measure in an efficient manner a transit time, for example a digestive transit, for example at the level of a digestive segment, for example gastric or intestinal or colonic. This device 1 may in particular be suitable for making it possible to measure in an efficient manner short transit times, that is to say less than twelve hours, and/or long transit times, that is to say greater than seventy two hours, by resorting to several devices ingested at different moments separated by time intervals suitable for this measurement.

RFID Markers

The plurality of RFID markers 11 of the device 1 consists for example in at least two RFID markers 11, preferably at least three RFID markers 11, for example more than three RFID markers 11, for example at least five RFID markers, for example more than five RFID markers 11, for example at least ten, for example more than ten. The plurality of RFID markers 11 makes it possible to obtain a mean measurement and thus to be able to disregard random factors that it is not wished to measure, as indicated previously.

Each RFID marker 11 may have dimensions such that at least one dimension is less than or equal to 15 mm, for example less than or equal to 5 mm, for example strictly less than 5 mm, for example less than or equal to 4 mm, for example strictly less than 4 mm.

Each RFID marker 11 may have dimensions such that the largest dimension of each RFID marker is less than or equal to 15 mm, for example less than or equal to 10 mm, and/or the smallest dimension of each RFID marker is less than or equal to 3 mm.

They are advantageously cylindrical.

It is in fact possible to produce RFID markers 11 of small size so as to include therein the desired number in a device 1 of which the size remains sufficiently small to be ingested.

Each RFID marker 11 may have a density greater than or equal to 1.20, for example less than or equal to 1.70, for example comprised between 1.20 and 1.70, for example comprised between 1.40 and 1.50. The density of each RFID marker 11 may thereby be comparable with that of other elements in transit, for example the digestive chyme, and thus pass through the digestive system at comparable times. Moreover, the result is a dilution of the RFID markers in the digestive chyme which makes it possible not to stimulate the digestive musculature by a distension, and thus to have a limited impact on the digestion during the measurement.

In other words, the RFID markers 11 mark the digestive chyme and no other support (medicine, sensor). It is thereby important that the RFID markers 11 are released from the device 1 in the chosen zone before reaching the studied digestive chyme. Indeed, RFID markers not released from their device ingested by the subject, as described in the prior art (US 2006/169292), would not make it possible to mark the digestive chyme but could have the aim of monitoring the movement of the device ingested in the digestive system of the subject at different speeds of the digestive chyme.

Each RFID marker 11 may for example comprise an antenna and a silicon chip. Each RFID marker 11 may for example comprise a substrate and/or an encapsulation. For example, here the RFID markers each comprise a cylindrical copper spool antenna enclosed in a cylindrical glass capsule, like tags intended for animal 'implantation.

The encapsulation may be adapted to extend around other elements of the RFID marker 11 so as to form a hermetic protection resistant to the environments of the digestive system, typically to acid or alkaline environments. The encapsulation is for example made of a biocompatible material, for example biocompatible glass.

In other words, the RFID markers are housed together in a disintegration matrix, but isolated from each other, each marker having its own encapsulation with a biocompatible material to protect it from acid or alkaline environments.

Each RFID marker 11 may be a passive RFID marker, for example a RFID marker 11 not comprising a battery and/or radiofrequency transmitter. Passive RFID marker is taken to mean a RFID marker suitable for back-modulating a wave so as to transmit information.

The passive RFID marker may for example use energy from the electromagnetic and/or magnetic wave received for its own supply.

The passive RFID marker is for example activated by the waves received.

The passive RFID marker is for example a class 0 or 1 passive RFID marker, that is to say that it is a read-only RFID marker. The passive RFID marker is for example a class 2 passive RFID marker, that is to say that it is suitable for carrying out functions other than reading, for example writing on a memory of the RFID marker.

It is thereby possible to use simpler, smaller and more robust RFID markers 11, without having to be concerned with the operating time of the battery. This small size combined with the plurality of RFID markers 11 enables a better representativeness of the transit.

Each RFID marker 11 may have an operating frequency less than or equal to 135 kHz, preferably comprised between 125 kHz and 135 kHz. Such a frequency is not perturbed by the human body, enables an operation without risk for the patient, and is easy to detect when the RFID marker is inside the body of the patient.

Each RFID marker 11 differs from the other RFID markers of the plurality of RFID markers 11 by a characteristic to differentiate each RFID marker 11 from the other RFID markers 11 of the plurality of RFID markers 11. The differentiation characteristic comprises for example the transmission frequency of each RFID marker 11, and/or the frequency at which each RFID marker 11 repeats a response signal. The differentiation characteristic may be chosen in such a way that all the RFID markers 11 respond to a same signal but that the response is different for each RFID marker while being readable simultaneously by a same network of RFID antenna.

Each RFID marker 11 may in particular use anticollision means to differentiate each RFID marker from the other RFID markers of the plurality of RFID markers. These anticollision means are for example implemented by means of an anticollision protocol recorded in a memory of the RFID marker 11.

The use of such a characteristic to differentiate one RFID marker 11 from another, or such anticollision means, enables for example a monitoring in real time of the digestive transit. It is thereby in particular possible to monitor each RFID marker 11 in an individualised manner and to deduce therefrom additional information. In particular, it is possible to identify an oversight in orally ingesting a device 1 in the case of a measurement requiring several ingestions of devices 1.

It is thereby also possible to measure a potential backpropagation of one or more RFID markers 11, that is to say a propagation in the anal-oral sense. This makes it possible to identify certain types of constipation otherwise impossible to characterise finely with markers such as radio-opaque markers.

Matrix

The matrix 12 may comprise a coating sensitive to acid pH. The coating is for example suitable for disintegrating at pHs less than 6.

The matrix 12 is for example suitable for disintegrating in an environment of a digestive segment, for example a gastric, intestinal or colonic environment. It is thereby possible to dimension the device 1 to choose the environment in which the RFID markers 11 will be released.

The matrix 12 is for example made of a mixture of gelatine, of animal or plant origin.

The matrix makes it possible to house the RFID markers, free to move in its envelope.

Detection Assembly

Figure 2A:
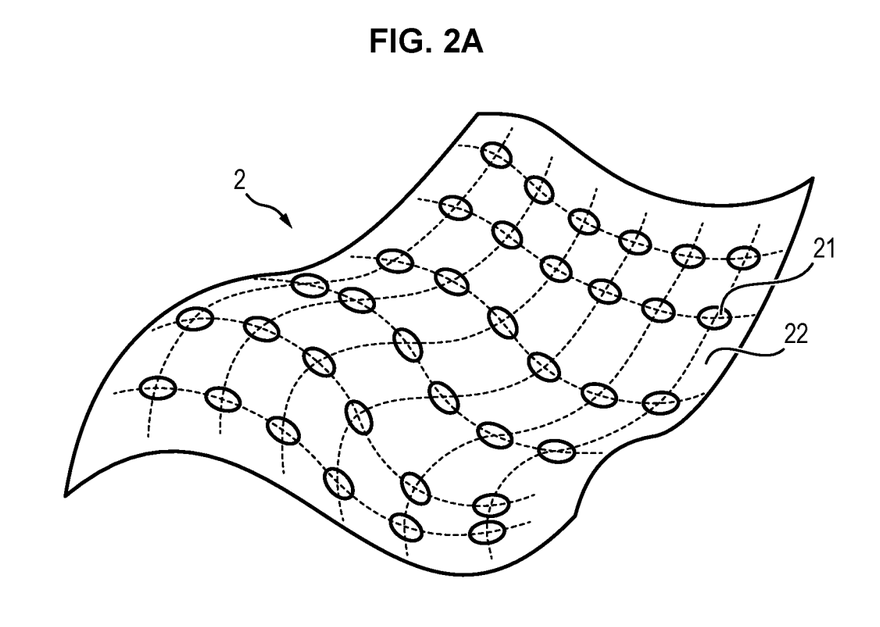
FIG. 2A represents a support according to an exemplary embodiment of the invention.
Figure 2B:
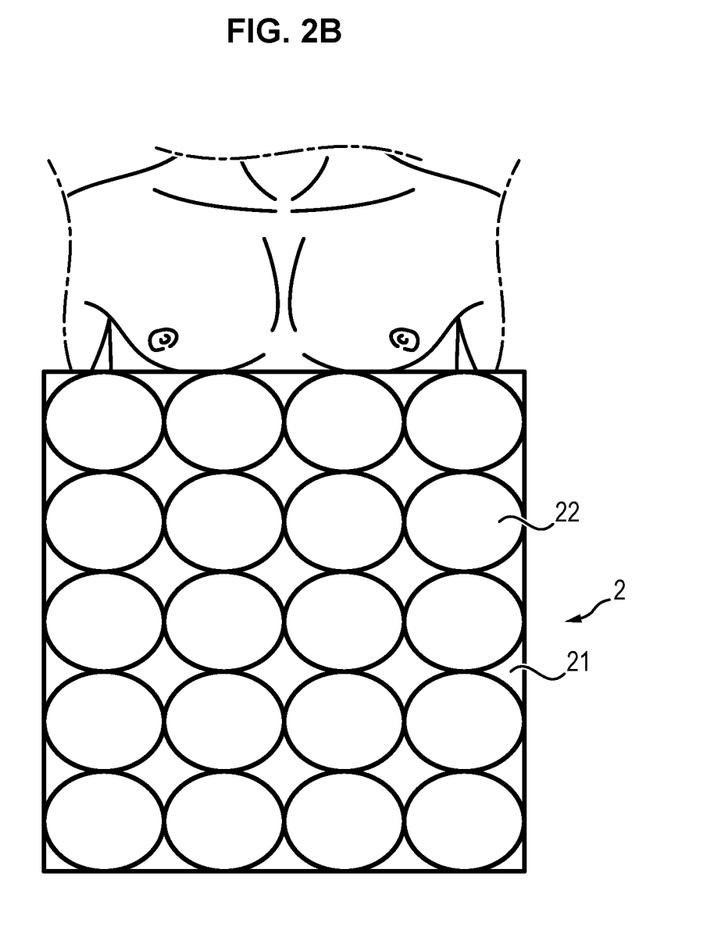
FIG. 2B represents the support of FIG. 2A covering the abdomen of a patient.

FIG. 2A represents a detection assembly 2 according to an exemplary embodiment of the invention. FIG. 2B represents the detection assembly 2 covering the abdomen of the patient.

General Structure of the Detection Assembly

The detection assembly comprises for example a detector 2 or is for example a detector 2.

The RFID signal detection assembly 2 is suitable for covering a part of the body of a patient. The detection assembly 2 comprises a support 22.

The reception support 2 is suitable for covering a part of the body of a patient.

The support 2 comprises a plurality of RFID antennas 21. The plurality of RFID antennas 21 is fixed to the support 22 so as to form a network, for example a network with the RFID antennas arranged in a contiguous manner. The network is suitable for identifying, when said support 22 covers the part of the body of the patient, the RFID markers 11 ingested by a patient when said support covers the part of the body of the patient.

To this end, the network is for example suitable for receiving, when said support 22 covers the part of the body of the patient, the RFID signals initially transmitted by at least one of the RFID antennas 21 and modulated by at least one of the RFID markers 11.

The same detection assembly 2 may thereby detect signals coming from several RFID markers 11 arranged in a same part of the body.

The detection assembly 2 may be suitable to make it possible to localise the different RFID markers 11. Indeed, the treatment of the responses of the different RFID antennas 21 may enable such a localisation, for example by triangulation.

The transmission power of each RFID antenna 21 may also be variable so as to be able to modify the reading distance of the RFID antenna 21 and to enable a more precise localisation.

Such a detection assembly 2 is not as such dangerous to health, and the associated measuring method also has considerably reduced health risks compared to those generated by measurement methods using radio-opaque markers, because it makes it possible to limit the irradiation of the patient to non-ionising radiation, because no radiography is necessary to detect the RFID markers 11. The detection assembly 2 operates for example by transmitting electromagnetic waves of low frequency type.

This detection assembly 2 is not based on magnetic field detection. The detection by the detection assembly 2 may thus be implemented in out-patient care because, unlike magnetic field detection, it is not sensitive to environmental electromagnetic perturbations and does not require bulky equipment.

In particular, it is not necessary that the RFID markers comprise a battery and/or a radiofrequency transmitter, a passive RFID marker being able to be used.

Its simplicity and low level of dangerousness enable the use of this detection assembly 2 for pregnant women or child patients. Moreover, the measurement associated with this detection assembly 2 may be carried out by an attending physician, a general practitioner or gastroenterologist, without requiring the presence of a radiologist.

This detection assembly 2 may in particular be suitable to make it possible to measure in an efficient manner a transit time, for example the digestive transit, for example at the level of a digestive segment, for example gastric or intestinal or colonic. This detection assembly 2 may in particular be suitable to make it possible to measure in an efficient manner short transit times, that is to say less than twelve hours, and/or long transit times, that is to say greater than seventy two hours, while resorting to several RFID markers 11 ingested at different moments separated by time intervals that are determined for this purpose.

The network of the detection assembly 2 is for example suitable for identifying independent RFID markers 11 coming from the device 1 described previously and ingested by a patient when said detection assembly 2 covers the part of the body of the patient.

To this end, the network is for example suitable for receiving, when said support 22 covers the part of the body of the patient, RFID signals initially transmitted by at least one of the RFID antennas 21 and modulated by at least one of the independent RFID markers 11 coming from the device 1 described previously and ingested by a patient when said detection assembly 2 covers the part of the body of the patient.

Support

The support 22 may have a shape that may be modified to hug the shape of the part of the body of the patient. It is thereby possible to form a detection network that is the closest to the RFID markers 11, which enables better detection thereof. The support 22 is for example flexible. The support 22 may for example form a cover.

The support 22 may be suitable for enabling several reading angles for the RFID antennas 21, which makes it possible to avoid blind spots. The support 22 may for example be suitable for following the curves of the abdomen of the patient and thereby have several antenna orientations.

The support 22 comprises for example a protective layer from external electromagnetic interference. The support 22 thus protects the network from undesired electromagnetic interference to make it possible to identify the RFID markers 11.

The support 22 comprises for example a hypoallergenic and/or biocompatible material, for example cotton and/or a synthetic hypoallergenic material.

The support 22 is for example associated with a surface for reflecting electromagnetic waves placed on another part of the body of the patient and intended to reflect the RFID signals, so as to improve the reading distance.

RFID Antennas

The plurality of RFID antennas 21 is for example suitable so that each RFID antenna 21 of said plurality of RFID antennas 21 can be connected to a same reading means (not represented), for example by multiplexing, so that the reading means (not represented) and the detection assembly 2 form a single RFID reader.

Alternatively, the plurality of RFID antennas 21 may be adapted so that at least one first RFID antenna 21 of the plurality of RFID antennas 21 can be connected to a first reader and that at least one second RFID antenna of the plurality of RFID antennas 21 can be connected to a different reader.

The plurality of RFID antennas 21 may be composed of at least three RFID antennas, for example more than three RFID antennas, for example at least six RFID antennas, for example more than six RFID antennas, for example at least ten RFID antennas 21. It is thereby possible to obtain a network enabling a fine detection of the localisation of each RFID marker 11 in the part of the body of the patient.

In particular, the RFID antennas 21 may be organised in such a way that an associated multiplexing enables better detection of the RFID markers 11.

The RFID antennas 21 may have a characteristic size comprised between 10 and 30 cm, for example between 15 and 25 cm.

The detection assembly 2 may comprise a longitudinal axis placed at the centre of the support 22, for example a central axis to lateralise the position of the RFID markers 21 and thereby to serve in the positioning on the body of the detection assembly. For example each RFID antenna 21 may be associated with a right or left portion of the body of the patient.

Each RFID antenna 21 has for example a predetermined transmission/reception range and is arranged in such a way that the network enables at least one transmission/reception range overlap zone, for example a plurality of transmission/reception range overlap zones.

Each RFID antenna 21 is for example a multidirectional antenna, which enables a more efficient detection of the RFID markers 11.

At least one RFID antenna 21, for example each RFID antenna 21, may be a spiral antenna.

The cover, which is for example a flexible cover, may be situated at a distance from the body of the patient, given the frequency of the waves used by the antennas, for example 135 kHz, close to the radio waves which pass through the body without being too attenuated and may be received after their reflection on the RFID markers at a distance for example of 20 cm between the RFID markers and the RFID antennas.

System

Figure 3:
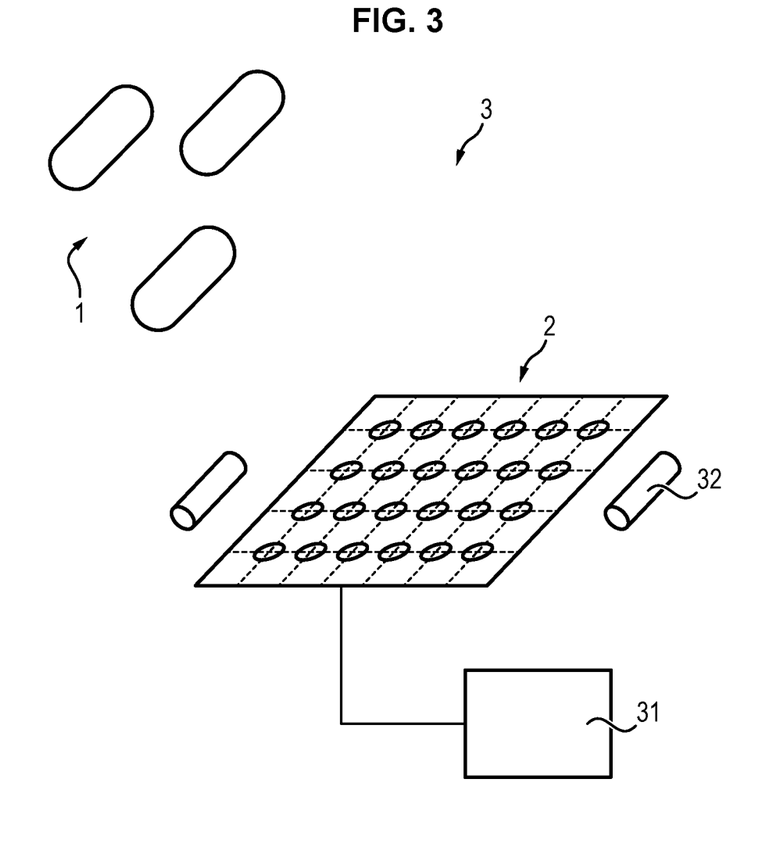
FIG. 3 represents a device according to an exemplary embodiment of the invention.

FIG. 3 represents a system 3 according to an exemplary embodiment of the invention.

The system 3 comprises:
at least one device 1 such as described previously,
a detection assembly 2 suitable for identifying the RFID markers 11 of the device 1 after ingestion by the patient of the device 1, for example such a detection assembly 2 comprising a network of RFID antennas 21, the detection assembly 2 being for example such as described previously, and
computing means 31 suitable for determining, by means of the detection assembly 2 of the system 3 and after ingestion by the patient of the device 1, a spatial distribution of RFID markers in the part of the body of the patient.

The combination of the device 1 and the detection assembly 2 is particularly efficient for the aforesaid reasons.

Alternatively, the system 3 comprises:
a plurality of RFID markers 11, for example in the form of the device 1 such as described previously,
a RFID signal detection assembly 2 suitable for covering a part of the body of a patient such as described previously, here the abdomen, and
computing means 31 suitable for determining, when the support 22 covers a part of the body of the patient and after ingestion of the RFID markers 11 by the patient, a spatial distribution of RFID markers 11 in the segment of the digestive system of the patient so as to enable a counting of the RFID markers (11) for each segment of the digestive system.

The combination of the device 1 and the detection assembly 2 is particularly efficient for the aforesaid reasons.

The result is thereby a system having few health risks, easy to implement and having better measurement sensitivity.

The system 3 may comprise at least one other external RFID marker 32 suitable to being positioned on the body of the patient to calibrate the position of the detection assembly 2, for example two such external RFID markers 32. It is thereby possible to improve further the detection of the RFID markers 11, for example by calibrating the network of RFID antennas 21. It is thereby possible to define the precise anatomical limits of zones of interest. This also makes it possible to carry out precise gastric emptying measurements with the system.

The computing means 31 may be configured to determine a measurement of the digestive transit time of the patient.

The computing means 31 may be configured to determine a representation of the digestive transit of the patient.

The computing means 31 comprise for example multiplexing means (not represented) suitable for commanding sequentially the activation of the antennas, for example one RFID antenna after the other, which makes it possible to localise the RFID markers and makes it possible to increase the precision of the counting of the RFID markers (in fact in the case where a first antenna detects a sensor already detected by another second antenna, it does not count it). The multiplexing means comprise for example an electronic multiplexing unit, for example a multiplexer.

The computing means 31 comprise for example reading means suitable for receiving a signal coming from at least one of the RFID antennas 22 of the detection assembly 2, and for decoding said signal received and for transmitting an identification of the RFID marker 11 coming from the decoded signal.

The computing means 31 may for example comprise a computing unit (not represented) comprising a memory suitable for storing a computer programme and a processor suitable for implementing said computer programme. The computing unit is for example suitable for receiving the identification of the RFID marker 11 transmitted. The computer programme is for example suitable for storing the identification of the RFID marker 11 and/or for commanding the multiplexing means so as to organise the multiplexing and/or for commanding the detection assembly 2 so as to select the intensity of an electromagnetic field transmitted by the RFID antenna(s) 22.

Method

Figure 4:
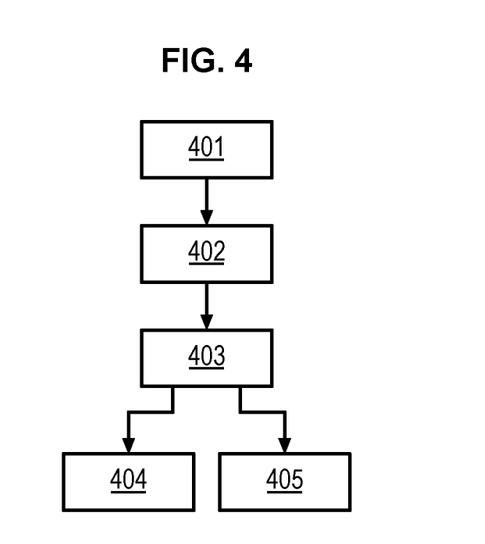
FIG. 4 represents a method according to an exemplary embodiment of the invention.

FIG. 4 represents a measurement method 4 according to an exemplary embodiment of the invention.

The measurement method 4 is implemented by means of a system such as described previously.

The measurement protocol copies that of the measurement of the colonic transit time using radio-opaque markers and which uses the counting of radio-opaque markers.

The measurement method comprises:
- putting in place 401 the support 22 so as to cover a part of the body of the patient;
- the reception 402, by the network, of RFID signals transmitted by the RFID markers 11; and
- the determination 403 by the computing means 31 of the spatial distribution of the RFID markers 11 in the part of the body of the patient, so as to enable a counting of the RFID markers (11) for each segment of the digestive system of the patient.

The determination 403 comprises for example a localisation of the RFID markers 11 on a virtual map of a part of the body of the patient, for example of the abdomen. This virtual map may be a virtual map acquired previously, for example a standard virtual map of a part of the body, or a virtual map of the part of the body of the patient acquired by prior measurement on the patient or acquired in real time.

The grid pattern or network of antennas of the cover makes it possible to define the virtual map of the part of the patient, here the abdomen; for example, once the cover has been laid on the abdomen, the antennas situated on the left, respectively right, part of the cover, correspond to the right, respectively left, colon and the antennas situated in the lower part of the cover correspond to the terminal bowel or rectosigmoid.

Thus, it is possible thanks to the method to count the markers per zone of the virtual map, which is going to make it possible to measure the total and segmental colonic transit time CTT.

The method 4 may further comprise the determination 404 by the computing means 31 of a measurement of the digestive transit time of the patient, for example the colonic transit time, for example the total and/or segmental colonic transit time, or the gastric emptying time.

For example, table 1 below represents the measurement of the colonic transit time carried out on 3 healthy subjects according to the invention.

TABLE 1

Measurement of the colonic transit time using the RFIDTRANSIT system. Validation of the feasibility on 3 healthy volunteers.

| Protocol | Ingestion of 20 RFID markers on D0 and daily detection of the number of markers present in the abdomen. |
| --- | --- |
| Calculation | The segmental colonic transit time is equal to CTT = 1/N $\Sigma[N_i((t_{i+1}-t_{i-1})/2)]$ and expressed in hours in the table below; its calculation is: $N_i$ number of RFID markers localised on day i; N number of RFID markers ingested; $t_i$ is the time after ingestion of the bolus of markers |

Results

| Subject | Day | Right colon | Left colon | Rectosigmoid | Total |
| --- | --- | --- | --- | --- | --- |
| 1 | 1 | 12 | 2.4 | 0 | 14.4 |
| 1 | 2 | 0 | 12 | 0 | 12 |
| 1 | 3 | 0 | 12 | 0 | 12 |
| 1 | 4 | 0 | 0 | 0 | 0 |
| | Total | 12 | 26.4 | 0 | 36.4 |
| 2 | 1 | 7.2 | 7.2 | 0 | 14.4 |
| 2 | 2 | 4.8 | 9.6 | 0 | 14.4 |
| 2 | 3 | 0 | 7.2 | 0 | 7.2 |
| 2 | 4 | 0 | 0 | 0 | 0 |
| | Total | 12 | 24 | 0 | 36 |
| 3 | 1 | 9.6 | 4.8 | 0 | 14.4 |
| 3 | 2 | 2.4 | 0 | 0 | 2.4 |
| 3 | 3 | 0 | 0 | 0 | 0 |
| | Total | 12 | 4.8 | 0 | 14.8 |

A so-called normal total colonic transit lies between 12 and 65 h. Beyond this, the subject has a very long colonic transit time. Below this, the subject has a very short colonic transit time.

The method 4 may further comprise the determination 405 by the computing means 31 of a representation of the digestive transit of the patient. The method 4 may further comprise the display 406 on a terminal 34 of the representation of the digestive transit of the patient.

Figure 5:
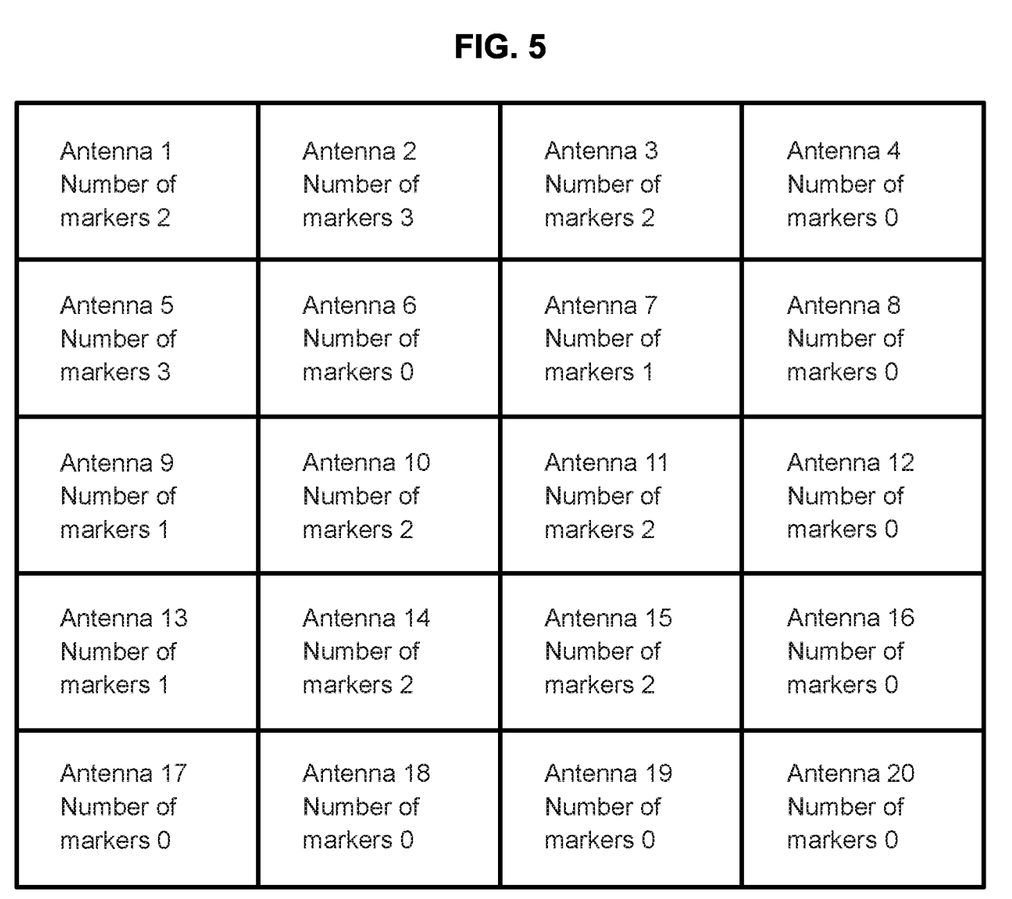
FIG. 5 represents an example of spatial distribution and counting of RFID markers in the digestive system of a healthy patient.

FIG. 5 represents an example of spatial distribution of RFID markers in the digestive system of a healthy patient according to the invention. In this patient, 12 RFID markers have been ingested each day for 6 days. The measurement is carried out on the 7$^{th}$ day at the time of the ingestion of the RFID markers. The colonic transit time in each zone of interest is computed according to the formula CTT=n $\Delta$T/N where:
- CTT is the transit time in the zone of interest (right colon, left colon, rectosigmoid or oral-anal)
- n is the number of RFID markers in the zone of interest
- N is the number of RFID markers ingested at each intake (here N=12)
- $\Delta$T is the time interval between 2 intakes of RFID markers (here 24 hours)

| Zone | Number of RFID markers detected | Colonic transit time (hours) |
| --- | --- | --- |
| Right colon | 11 | 22 |
| Left colon | 5 | 10 |
| Rectosigmoid | 5 | 10 |
| Total | 21 | 42 |

Such a method enables the evaluation of the efficacy of a medicated treatment of which the indication would be to modify the colonic transit or to improve the symptoms associated with colopathy, not just for the clinical monitoring of patients but also within the context of the evaluation of a new medicine.

The method may comprise either the single ingestion of a device 1, or the ingestion of several devices 1 at different times by the patient, in harmony with the methods for measuring the colonic transit time described previously such as "Single marker-Single ingestion-Multiple films" or "Multiple markers-Multiple ingestion-Multiple films" or "Single marker-Multiple ingestion-Single film", preferentially "Single marker-Multiple ingestion-Single film" or "Multiple markers-Multiple ingestion-Single film".

In the case of ingestion of several devices 1, the ingestion may be carried out several times in succession, for example separated in time of the order of 12 h, for example for several days, for example for 6 or 7 days.

The determination 403 of the localisation of the RFID markers 11 using the device 22 may take place either at a precise time, for example after 7 days after the ingestion of the device 1, or at different times after the ingestion of the device 1, for example every 24 h for 7 days.

The computing means 31 determine the total colonic transit time equal to $CTT=\Delta T \cdot \Sigma N_i/N$ in the case where several devices 1 are ingested at different times and their localisations using the device 22 determined at a single time after the ingestion of the device 1. With $N_i$ the number of RFID markers on day i, N the number of RFID markers ingested, $\Delta T$ is the time interval between two ingestions of device 1 and expressed in hours.

The computing means 31 determine the total colonic transit time equal to $CTT=1/N \; \Sigma[N_i \; ((t_{i+1}-t_{i-1})/2)]$ in the case where a device 1 is ingested at a single time and its localisation using the device 22 is determined at different times $t_i$ after the ingestion of the device 1.

With $N_i$ the number of RFID markers localised on day i, N the number of RFID markers ingested, $(t_{i+1}-t_{i-1})/2$ is the average time interval in hours between two measurements carried out at times $t_{i+1}$ and $t_{i-1}$ The determination takes place by sub-dividing the abdomen of the patient into 3 segments: right colon, left colon and terminal bowel or rectosigmoid to determine so-called progression constipations, and secondary constipations with an evacuation problem.

The measurement may take place on a patient who has fasted and after a meal in order to determine the role of diet on the digestive function, notably in the case of irritable bowel syndrome or constipation.

Advantageously, the method may enable:
after an ingestion every day of a device 1 by a patient, the counting of the RFID markers on a given day (for example the ingestion of 12 markers every day at a regular time for 6 days and measurement on the 7$^{th}$ day);
after an ingestion on a single day of a device 1, the counting of the RFID markers for several days in succession to monitor the movement of the RFID markers of the device,
the identification of the RFID markers enables the determination of the transit time of the RFID markers after ingestion on day i and thus the calculation of the average transit of a RFID marker while considering the state of the subject stable and by considering the variability of the colonic transit.

The invention claimed is:

1. An assembly for studying the digestive transit of the patient and determining a measurement of the digestive transit time of the patient and a spatial representation of the digestive transit of the patient by determining a number of RFID markers for each segment of the digestive system at each different instant, comprising:
at least one device, suitable for being ingested by a patient, and intended to determine a measurement of the digestive transit time of the patient and a spatial representation of the digestive transit of the patient at given instants, the at least one device comprising
a disintegration matrix that is designed to disintegrate in a digestive segment and a plurality of independent passive RFID marker that are housed together in the disintegration matrix,
when the disintegration matrix disintegrates itself, the RFID markers move away from each other, so that each RFID marker is able to move independently of the other RFID markers,
each RFID marker being, in the disintegration matrix, protected by a hermetic encapsulation in a biocompatible material and resistant to an environment of a digestive system, to mark the movement of the digestive chyme in the segments of the digestive system to have a measurement of the digestive transit time of the patient and a spatial representation of the digestive transit of the patient at given instants;
the assembly for studying the digestive transit further comprising a detection assembly suitable for covering the whole of the abdomen of a patient, the detection assembly comprising a support and a plurality of RFID antennas with transmission/reception and fixed to the support so as to form a network, the network being suitable for identifying, when said support covers the patient, RFID markers of at least one device, suitable for being ingested by a patient, and intended to determine a measurement of the digestive transit time of the patient and a spatial representation of the digestive transit of the patient at given instants, the RFID antennas being spiral antennas, and the network being a grid pattern of contiguous antennas so as to detect a transmission of the RFID markers;
the assembly for studying the digestive transit further comprising means for computing connected to the RFID antennas, the means for computing for determining, by detection assembly and after ingestion of the device by the patient, a spatial distribution of the passive and independent RFID markers, in one or more segments of the digestive system of the patient,
wherein the means for computing are configured to determine the number of RFID markers for each segment of the digestive system at given instants and
wherein the means for computing are configured to determine a measurement of the digestive transit time of the patient and a spatial representation of the digestive transit of the patient at given instants, by the reception of an identification signal by the RFID antennas, the identification signal being sent by the RFID markers situated under the RFID antennas,
wherein the identification signal results from the signal sent by each RFID antenna and reflected by each RFID marker situated under the RFID antennas, each RFID marker having been moved independently of the other RFID markers in the digestive segments,
the means for computing comprising means for multiplexing for commanding sequentially an activation of the RFID antennas, one RFID antenna after the other, the RFID antennas receiving the identification signal sent by the RFID markers, the identification signal results from the signal sent by each RFID antenna and reflected by each RFID marker situated under the RFID antenna.

2. The assembly according to claim 1, wherein the means for computing comprise means for identification which are suitable for receiving a signal coming from the RFID antennas of the detection assembly and for decoding said received signal and transmitting an identification of the RFID marker coming from the decoded signal, in order not to count twice the same RFID marker by two different RFID antennas during the sequential command.

3. The assembly according to claim 1, wherein the support is a flexible cover including antennas for stimulation and detection for detecting, at a distance from the body, the RFID markers.

4. The assembly according to claim 1, wherein the disintegration matrix forms a hard capsule, capsule, pessary or tablet housing the RFID markers.

5. The assembly according to claim 1, wherein the RFID markers are free to move with respect to each other in the matrix which is a hard capsule or capsule.

6. The assembly according to claim 1, wherein the device comprises more than 4 RFID markers.

7. The assembly according to claim 1, wherein the RFID markers have a density between 1.20 and 1.70, relative to the density of water.

8. The assembly according to claim 1, wherein the RFID markers are cylindrical and have a length less than or equal to 15 mm and a diameter less than or equal to 3 mm.

9. The assembly according to claim 1, wherein the RFID markers reflect a frequency less than or equal to 135 kHz.

10. The assembly according to claim 1, in which the detection assembly comprises a protective layer from external electromagnetic interference.

11. The assembly according to claim 1, the assembly comprises a surface for reflecting magnetic electromagnetic waves configured to be disposed on a part of the body of the patient.

12. A method for studying the digestive transit of the patient and determining a measurement of the digestive transit time of the patient and a spatial representation of the digestive transit of the patient at given instants, implemented by means of an assembly according to claim 1, comprising:
putting in place the detection assembly so as to cover the whole of the abdomen of the patient;
the ingestion of at least one device by a patient on a given day,
the reception, by the network of the detection assembly, and the identification of the RFID markers coming from the device;
the determination, by the means for computing connected to the RFID antennas with transmission/reception, of the spatial distribution of the RFID markers in one or more segments of the digestive system of the patient, so as to enable a count of the RFID markers for each segment of the digestive system and to determine a measurement of the digestive transit time of the patient and a spatial representation of the digestive transit of the patient at given instants,
by the reception of an identification signal by the RFID antennas, the identification signal being sent by the RFID markers situated under the RFID antennas, and the identification signal is a reply to the signal sent by each RFID antenna and received by each RFID marker situated under the RFID antenna,
each RFID marker having been moved independently of the other RFID markers in the digestive segment(s).

13. The method according to claim 12, in which:
the RFID antennas are activated one after the other sequentially, one RFID antenna
after the other, the RFID antennas receiving an identification signal sent by the RFID markers, and which follows the signal sent by each RFID antenna and received by each RFID marker situated under the RFID antenna,
the RFID markers are identified to be counted a single time by a single RFID antenna.

14. The method according to claim 13, wherein the disintegration matrix presents RFID markers, and is without a medicine, or without internal physiological measurement sensor.

15. The method according to claim 12, wherein the segments of the digestive system concern the abdomen and wherein the determination takes place by subdividing the abdomen of the patient into at least 3 segments: right colon, left colon and rectosigmoid for the measurement of the colonic transit time or a segment for the measurement of gastric emptying.

16. The method according to claim 12, wherein the ingestion is carried out with at least one device ingested by a patient on one day or for several days in succession and wherein the number of RFID markers is measured and counted, in each segment of the digestive system, on one given day or on several given days.

* * * * *